United States Patent [19]

Nagashima et al.

[11] 4,444,982
[45] Apr. 24, 1984

[54] (+)- OR (−)-7-HYDROXYMETHYL-2,6,6-TRIMETHYLTRICYCLO[6,2,1,0$^{1,5}$]UNDECANE

[75] Inventors: Tsukasa Nagashima, Tokyo; Toshio Yoshida, Kanagawa, both of Japan

[73] Assignee: Takasago Perfumery Co., Ltd., Tokyo, Japan

[21] Appl. No.: 427,345

[22] Filed: Sep. 29, 1982

[30] Foreign Application Priority Data

Nov. 5, 1981 [JP] Japan .................................. 56-177480

[51] Int. Cl.$^3$ ............................................. C07C 35/22
[52] U.S. Cl. .................................................. 568/817
[58] Field of Search .......................................... 568/817

[56] References Cited

U.S. PATENT DOCUMENTS 4,142,997 3/1979 Maurer ................................. 568/817
4,311,852 1/1982 Skorianez ............................. 568/817

OTHER PUBLICATIONS

Jain et al., "Tetrahedron Letters", No. 9, pp. 13–17, (1959) Pergamon Press, Great Britain.
Maheshwari et al., "Tetrahedron", (1963), vol. 19, pp. 1079–1090 and 1519–1525, Pergamon Press, Printed in Northern Ireland.
Varma et al., "Tetrahedron", (1965), vol. 21, pp. 115–138, Pergamon Press.
Nakanishi et al., "Phytochemistry", vol. 20, No. 7, pp. 1597–1599, (1981), printed in Great Britain.
Japanese Chemical Society, Journal, vol. 56p, 1155, (1935).

Primary Examiner—Werren B. Lone
Attorney, Agent, or Firm—Sughrue, Mion, Zinn, Macpeak, & Seas

[57] ABSTRACT (+)- or (−)-7-hydroxymethyl-2,6,6-trimethyltricyclo[6,2,1,0$^{1,5}$]undecane represented by the following formula (I) or (II):

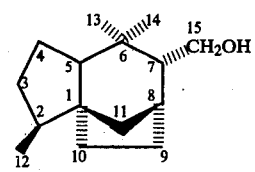

(I)

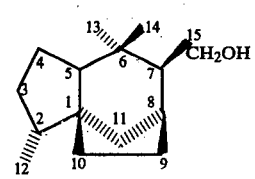

(II)

1 Claim, No Drawings

(+)- OR (−)-7-HYDROXYMETHYL-2,6,6-TRIMETHYL-TRICYCLO[6,2,1,0^{1,5}]UNDECANE

FIELD OF THE INVENTION

This invention relates to novel 7-hydroxymethyl-2,6,6-trimethyl-tricyclo[6,2,1,0^{1,5}]undecane compounds represented by the following formula (I) or (II):

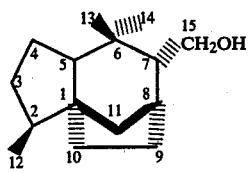
(I)

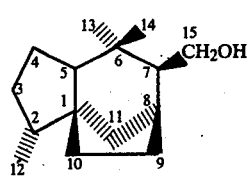
(II)

BACKGROUND OF THE INVENTION

Agarwood, which has long been famous as a natural perfume, is formed as a reslt of the resinification of terpenes contained in old trees of *Aquillaria agallocha* Roxb. growing in India or Southeast Asia by the action of a certain kind of bacteria to give "oriental" odor. Many studies have been made on the scent-providing compounds of agarwood, and the presence of benzylacetone, p-methoxybenzylacetone, hydrocinnamic acid, p-methoxyhydrocinnamic fixed [Kafuku & Ichikawa, Journal of the Japanese Chemical Society, 56, 1155 (1935), Ichikawa & Ye, ibid., 60, 1247 (1939)], agarol (III) [J. C. Jain et al., Tetrahedron Letters, 13 (1959)], agarofuran (IV) [M. L. Maheshwari et al., Tetrahedron, 19, 1079 and 1519 (1963)], and agarospirol (V) [K. R. Varma et al., Tetrahedron, 21, 115 (1965)] has been found.

Recently, the presence of jinkohol (VI), a sesquiterpene alcohol of a prezizane derivative, has been reported [T. Nakanishi et al., Phytochemistry, 20, 7, 1597-1599 (1981)].

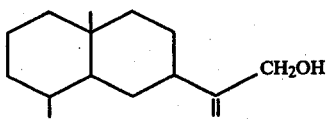
(III)

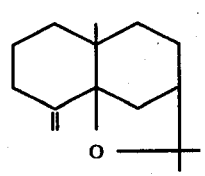
(IV)

(V)

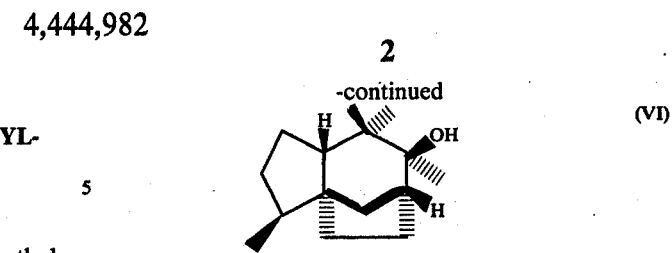
(VI)

SUMMARY OF THE INVENTION

As a result of continued studies on the scent-providing ingredients in agarwood to obtain high grade perfumes, the inventor has found that (+)-7-hydroxymethyl-2,6,6-trimethyltricyclo[6,2,1,0^{1,5}]undecane represented by formula (I) is one of the important compounds which provides the pleasant scent of agarwood, and that a stereoisomer thereof of formula (II) also provides the same scent, and that compounds of formulae (I) and (II) can be easily synthesized from (+)-prezizaene of formula (VII) and (−)-prezizaene of formula (VIII), respectively,

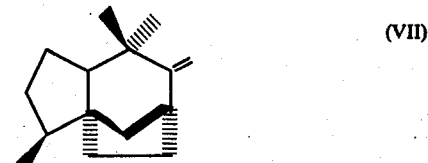
(VII)

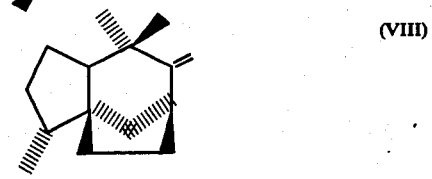
(VIII)

i.e., from (+)- or (−)-7-methylene-2,6,6-trimethyltricyclo[6,2,1,0^{1,5}]undecane, thus having achieved the present invention.

DETAILED DESCRIPTION OF THE INVENTION (+)-7-Hydroxy-2,6,6-trimethyltricyclo-[6,2,1,0^{1,5}]undecane of the formula (I) of the present invention can be synthesized according to the following process.

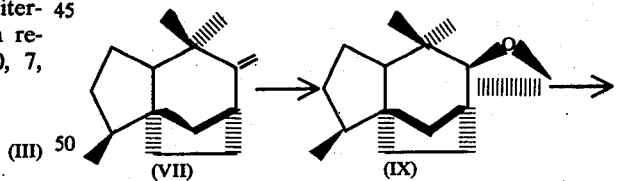

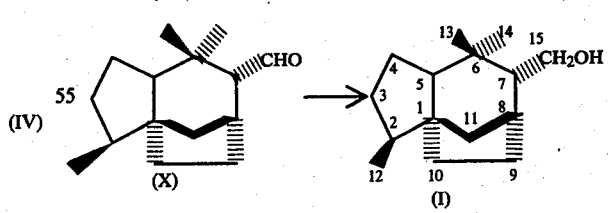

The starting material, (+)-prezizaene of formula (VII), can be obtained by dehydrating jinkohol of formula (VI), which is separated from agar oil by extraction and chromatography, i.e., 7-hydroxy-2,6,6,7-tetramethyl-tricyclo[6,2,1,0^{1,5}]undecane, in pyridine using phosphorus oxychloride as dehydrating agent [T. Nakanishi et al., Phytochemistry, 20, 7, 1597-1599 (1981)].

In practicing this process (+)-prezizaene of formula (VII) is first oxidized with an organic peracid such as peracetic acid or m-chloroperbenzoic acid in a solvent such as chloroform or dichloromethane to prepare an epoxide, 2,6,6-trimethyl-tricyclo[6,2,1,0$^{1,5}$]undecyl-7,15-epoxide of formula (IX). Since this reaction is an exothermic reaction, care must be taken not to allow the reaction to proceed rapidly and increase the temperature rapidly. For example, it is preferable to add and mix the starting materials at 5° C. or lower, and stir the resulting mixture at room temperature till completion of the reaction.

After completion of the reaction, an aqueous solution of sodium hydrogen sulfite is added thereto and, after further adding thereto an aqueous solution of alkali such as sodium carbonate to neutralize, the organic layer is washed with water, and dried, followed by concentrating the solvent under reduced pressure to obtain an epoxide as a residue. Then, this epoxide is heated together with silica gel for about 30 minutes in a saturated hydrocarbon solvent such as n-hexane to conduct isomerization to obtain the aldehyde, 7-formyl-2,6,6-trimethyl-tricyclo[6,2,1,0$^{1,5}$]undecane of formula (X).

After completion of the isomerization, silica gel and the solvent are removed, and the residue is used in a subsequent reducing step. In the reducing step, lithium aluminum hydride is used as a hydrogenating agent. This hydrogenating agent is kept at about 10° C. or lower together with a solvent such as ether, dioxane or tetrahydrofuran, and the 7-formyl-2,6,6-trimethyltricyclo[6,2,1,0$^{1,5}$]undecane is gradually added dropwise thereto.

After completion of the dropwise addition, the temperature of the reaction product is allowed to rise to room temperature, the reaction thus being completed.

Subsequent procedures are conducted in a conventional manner: The reaction mixture is treated successively with water and hydrochloric acid for inactivation of lithium aluminum hydride, then distilled to obtain the end product (+)-7-hydroxymethyl-2,6,6-trimethyl-tricyclo[6,2,1,0$^{1,5}$]undecane of formula (I). The theoretical yield of the product based on (+)-prezizaene is about 50 and 60%.

Another compound of the present invention, the compound of formula (II)

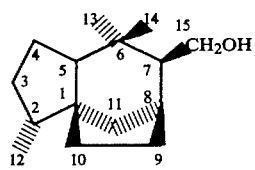
(II)

which is an isomer of the above described compound of formula (I), can be synthesized in the same manner as with the (+)-compound using as the starting material (−)-prezizaene of formula (VIII) which can be synthesized from readily available d-pulegone [Robert M. Coates et al., J. Org. Chem., 45, 26, 5430–5432 (1980)] or, alternatively, by dehydrating (−)-prezizanol of formula (XI) contained in high amounts in EREOPHILA GEORGEI, a type of sandalwood growing in Australia [Peter J. Carrol et al., Phytochemistry, 15, 777–780 (1976)].

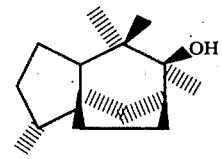
(XI)

The compound of formula (II) of the present invention can be obtained by subjecting (−)-prezizaene to the same epoxidation, isomerization, and reduction steps as in the case of using (+)-prezizaene as the starting material.

The thus obtained compounds of the present invention, (+)- and (−)-7-hydroxymethyl,2,6,6-trimethyl-tricyclo[6,2,1,0$^{1,5}$]undecane, represented by the formulae (I) and (II), respectively, give a similar odor, i.e., the woody note characteristic of sesquiterpenes in combination with a somewhat camphorous odor and, when heated or burnt, the characteristic odor of agarwood is strengthened. Thus, they can be compounded in various perfume compositions as perfume ingredients in a conventional manner. Particularly, they exhibit excellent effects when compounded in perfume compositions which are to be heated to give a scent, such as incense sticks, tobaccos, etc. In addition, they can be easily synthesized. Accordingly, they are extremely useful as perfume ingredients.

The present invention will now be described in more detail by the following examples of preferred embodiments of the present invention which, however, are not to be construed as limiting the present invention in any way.

EXAMPLE 1

50 ml of dichloromethane and 25.8 g (containing 0.12 mol) of m-chloroperbenzoic acid (purity: 80%) were placed in a 200-ml reaction flask and, while keeping the temperature at 0° to 5° C. by ice water, and 20.4 g (0.1 mol) of (+)-prezizaene of formula (VII) was dropwise added thereto over about two hours. After completion of the addition thereof, the reaction mixture was further stirred for one hour at room temperature. After completion of the reaction, the reaction mixture was washed successively with 50 ml of a 20% sodium hydrogen sulfite aqueous solution, 50 ml of a 5% sodium carbonate aqueous solution, and three times with 50 ml of water. After drying by anhydrous sodium sulfate, dichloromethane was distilled off under reduced pressure to obtain 20 g of the crude product 2,6,6-trimethyl-tricyclo[6,2,1,0$^{1,5}$]-undecyl-7,15-epoxide of formula (IX) as a residue. This crude product was then transferred to a 100-ml reaction flask, and 20 ml of n-hexane and 10 g of silica gel were placed therein, followed by heating to reflux n-hexane while stirring for 30 minutes. After cooling, 10 ml of ether was added thereto and the system stirred for 30 minutes. Then, the silica gel was removed by filtration, and the ether-hexane solution was concentrated under reduced pressure to obtain 18 g of crude aldehyde product, i.e., 7-formyl-2,6,6-trimethyl-tricyclo[6,2,1,0$^{1,5}$]-undecane of formula (X).

Then, 30 ml of ether and 3.8 g of lithium aluminum hydride were placed in a 200-ml reaction flask, and 18 g of the crude aldehyde obtained above was added thereto over about 2 hours while keeping the temperature at 0° to 10° C. by cooling with ice water from the outside, followed by stirring for one hour at room temperature to complete the reaction. Then, 5 ml of water was dropwise added thereto while keeping the solution temperature at room temperature and, after stirring for 1 hour, 100 ml of a 15% hydrochloric acid aqueous solution was added thereto and the mixture was stirred for 10 minutes at room temperature. The whole solution was transferred to a separating funnel and, after discarding the aqueous layer which was formed, washed twice with 50 ml of water, once with 50 ml of a 5% sodium carbonate aqueous solution, and three times with 50 ml of water, followed by drying the resulting ether layer using anhydrous sodium sulfate. This ether layer was concentrated and distilled under reduced pressure at 95° to 110° C./0.2 mm Hg to obtain 12 g of the compound of the present invention, (+)-7-hydroxymethyl-2,6,6-trimethyl-tricyclo[6,2,1,0$^{1,5}$]undecane of formula (I). The theoretical yield of the product based on (+)-prezizaene was 54%. Physical properties and values obtained by analysis of the product are as follows.

m.p.: 82° C.

Optical rotation: $[\alpha]_D^{25} + 27.3$

MS: M+222; m/e 189, 135, 95, 82

IR (KBr): 3220 cm$^{-1}$

NMR (CDCl$_3$), ($\delta_{ppm}$): 0.76 (s, 3H), 0.83 (d, 3H), 0.98 (s, 3H), 2.33 (m, 1H), 3.51 (t, 1H)

EXAMPLE 2

In the same manner as in Example 1 except for using (−)-prezizaene in place of (+)-prezizaene, there was obtained 11 g of the end product (−)-7-hydroxymethyl-2,6,6-trimethyl-tricyclo[6,2,1,0$^{1,5}$]undecane of formula (II) having a boiling point of 95° to 110° C/0.2 mm Hg from 20.4 g (0.1 mol) of (−)-prezizaene. The theoretical yield of the product based on (−)-prezizaene was 49.6%. Physical properties and values obtained by analysis of the product are as follows:

m.p.: 81° C.

Optical rotation: $[\alpha]_D^{25} - 25.2$

MS:M+222; m/e 189, 135, 95, 82

IR (KBr) (cm$^{-1}$): 3220

NMR (CDCl$_3$), ($\delta_{ppm}$): 0.76 (s, 3H), 0.83 (d, 3H), 0.98 (s, 3H), 2.33 (m, 1H), 3.51 (t, 1H)

EXAMPLE 3

A perfume for incense sticks was compounded according to the following formulation.

|  | parts by weight |
|---|---|
| Musk xylol | 105 |
| Musk ambrette | 93 |
| Vanillin | 13 |
| Heliotropin | 54 |
| Coumarin | 40 |
| Borneol | 27 |
| Methyl α-ionone | 145 |
| Eugenol | 40 |
| Cinnamic aldehyde | 13 |
| Benzyl alcohol | 470 |
|  | 1,000 |

To 10 g of the above compounded perfume was added 2.5 g of (+)-7-hydroxymethyl-2,6,6-trimethyl-tricyclo[6,2,1,0$^{1,5}$]undecane of formula (I) obtained in Example 1, and a paper to be perfumed was dipped therein. When the thus dipped paper was burnt, there was given a pleasant scent having a remarkably strengthened woody note as compared with a comparative paper dipped in a compounded perfume not containing the compound of formula (I) and an oriental note reminding one of shrines and temples.

EXAMPLE 4

A perfume for candles was compounded according to the following formulation.

|  | parts by weight |
|---|---|
| Benzyl acetone | 102 |
| p-Methoxybenzaldehyde | 80 |
| Cinnamic aldehyde | 70 |
| Guaiac wood oil | 250 |
| Eugenol | 100 |
| Patchouli oil | 120 |
| Vetiver oil | 150 |
| Santalol | 128 |
|  | 1,000 |

To 10 g of the above described compound perfume was added 1 g of (+)-7-hydroxymethyl-2,6,6-trimethyl-tricyclo[6,2,1,0$^{1,5}$]undecane of formula (I) obtained in Example 1. A professional perfumer approved that woody and oriental notes, characteristic of agarwood, were strengthened.

EXAMPLE 5

A Eau de Cologne was compounded according to the following formulation.

|  | parts by weight |
|---|---|
| Cedryl acetate | 303 |
| Sandalwood oil | 76 |
| Vetiver oil | 30 |
| Cedar wood oil | 30 |
| Cyclopentadecanolide | 30 |
| Ethylene brassylate | 106 |
| Oak moss absolute | 15 |
| Civet absolute | 8 |
| Phenylethyl alcohol | 243 |
| Benzyl acetate | 30 |
| Cinnamon leaf oil | 100 |
| Bergamot oil | 29 |
|  | 1,000 |

To 10 g of the above-described compound perfume was added 3.3 g of (−)-7-hydroxymethyl-2,6,6-trimethyltricyclo[6,2,1,0$^{1,5}$]undecane of formula (II) obtained in Example 2. A professional perfumer approved that the compounded perfume containing the compound of formula (II) have a remarkably strengthened woody and oriental note as compared with a comparative compounded perfume not containing the compound of formula (II).

EXAMPLE 6

A perfume was compounded according to the following formulation.

|  | parts by weight |
|---|---|
| Cedar wood oil | 200 |
| Sandalwood oil | 80 |
| Vetiver oil | 30 |
| Musk ambrette | 100 |
| Oak moss absolute | 20 |
| Civet absolute | 5 |
| Phenylethyl alcohol | 250 |
| Benzyl acetate | 100 |
| Patchouli oil | 110 |
| Bergamot oil | 105 |

| parts by weight |
| --- |
| 1,000 |

To 10 g of the above described compounded perfume was added 2.5 g of (−)-7-hydroxymethyl-2,6,6-trimethyltricyclo[6,2,1,0$^{1,5}$]undecane of the formula (II). The resulting compounded perfume gave a remarkably increased refined odor as compared with the compounded perfume of the same formulation except for not containing the compound of formula (II), and was therefore an excellent perfume for high grade perfumed water.

While the invention has been described in detail and with reference to specific embodiments thereof, it will be apparent to one skilled in the art that various changes and modifications can be made therein without departing from the spirit and scope thereof.

What is claimed is:

1. (+)- or (−)-7-hydroxymethyl-2,6,6-trimethyltricyclo[6,2,1,0$^{1,5}$]undecane represented by the following formula (I) or (II):

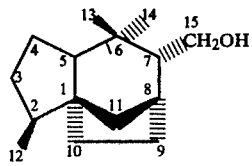

(I)

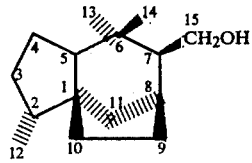

(II)

* * * * *